United States Patent [19]

Uthe

[11] 4,229,653
[45] Oct. 21, 1980

[54] METHOD AND APPARATUS FOR MONITORING PARTICULATE MASS CONCENTRATION OF EMISSIONS FROM STATIONARY SOURCES

[75] Inventor: Edward E. Uthe, Los Altos, Calif.
[73] Assignee: SRI International, Menlo Park, Calif.
[21] Appl. No.: 25,732
[22] Filed: Mar. 30, 1979
[51] Int. Cl.³ .............................................. G01J 1/00
[52] U.S. Cl. ................................... 250/339; 250/340; 250/343
[58] Field of Search ............... 250/339, 340, 341, 343

[56] References Cited
U.S. PATENT DOCUMENTS

| | | | |
|---|---|---|---|
| 3,736,421 | 5/1973 | Strange et al. | 250/341 |
| 4,135,092 | 1/1979 | Milly | 250/343 |

*Primary Examiner*—Davis L. Willis
*Attorney, Agent, or Firm*—Victor R. Beckman

[57] ABSTRACT

Method and apparatus for monitoring particulate mass concentration of emissions, such as fly ash, from a stationary source are disclosed which employ a single-wavelength infrared transmissometer. Emissions from a source, such as a fossil fueled power plant, generally contain particles of known material of a wide range of sizes. Often the particle size distribution varies during emission. In accordance with the present invention a single-wavelength transmissometer is employed which operates at a wavelength at which the extinction-to-mass concentration ratio as a function of particle size is substantially constant. Consequently, the transmissometer output provides a measure of the mass concentration of particulate material emitted from the source independent of the size of the particles. Logarithmic amplification of the transmissometer detector output provides a direct measure of the mass concentration.

10 Claims, 3 Drawing Figures

METHOD AND APPARATUS FOR MONITORING PARTICULATE MASS CONCENTRATION OF EMISSIONS FROM STATIONARY SOURCES

ORIGIN OF THE INVENTION

The invention described herein was made in the course of work under a contract with the U.S. Environmental Protection Agency.

BACKGROUND OF THE INVENTION

Particulate emissions from stationary sources are regulated by visible emission (opacity) and particulate mass concentration standards. Available white-light in-stack transmissometers are a reliable and relatively inexpensive means for monitoring opacity. The opacity-to-mass concentration relationship is strongly dependent on the size distribution of the scattering particles; therefore, opacity readings can be calibrated to provide reliable mass concentration readings only for sources where the particle size distribution is relatively constant. No similarly acceptable technique using transmissometry is currently available for monitoring mass concentration of particulate emissions.

Transmission data in the infrared energy range are shown in an article in APPLIED OPTICS, Vol. 16, No. 6 June 1977 entitled, "Infrared extinction spectra of some common liquid aerosols" by Hugh R. Carlon et al. In the article independency of the ratio of extinction coefficient to water content of fogs as a function of particle size for a particular wavelength used (12.5 $\mu$m) is noted. The present invention, however, distinguishes over the disclosure of the Carlon et al article in the use of a transmissometer wavelength at which the extinction coefficient-to-mass concentration ratio for typical pollution aerosols is substantially independent of the particle size. Pollution particles differ from fog particles in that they are normally smaller, of higher refractive index (real part) and may be irregular in shape.

SUMMARY OF THE INVENTION AND OBJECTS

An object of this invention is the provision of improved method and means for monitoring particulate mass concentration of emissions from a stationary source which are substantially independent of the particle size distribution of the emissions.

An object of this invention is the provision of an improved transmissometer and method of operating the same at a single wavelength selected to provide a measure of the mass concentration of the emitted particulate material substantially independent of the particle size distribution.

The above and other objects and advantages of this invention are achieved by use of a transmissometer comprising an energy source operating at the selected single wavelength, such as for a Helium-Neon laser having an output at 3.39 $\mu$m. The laser beam is directed through the pollutant aerosol, such as fly ash, along a path of predetermined length therein, and thence impinges upon an infrared detector filtered for the wavelength employed. The wavelength employed is selected such that the ratio of the extinction coefficient to the mass concentration of the particles is substantially independent of the particle size. As a result, the detector output provides a measure of the mass concentration independent of variation in the particle size distribution of the aerosol.

The invention as well as the above and other objects and advantages thereof, will become apparent from the following detailed description when considered with the accompanying drawings.

Figure 1:
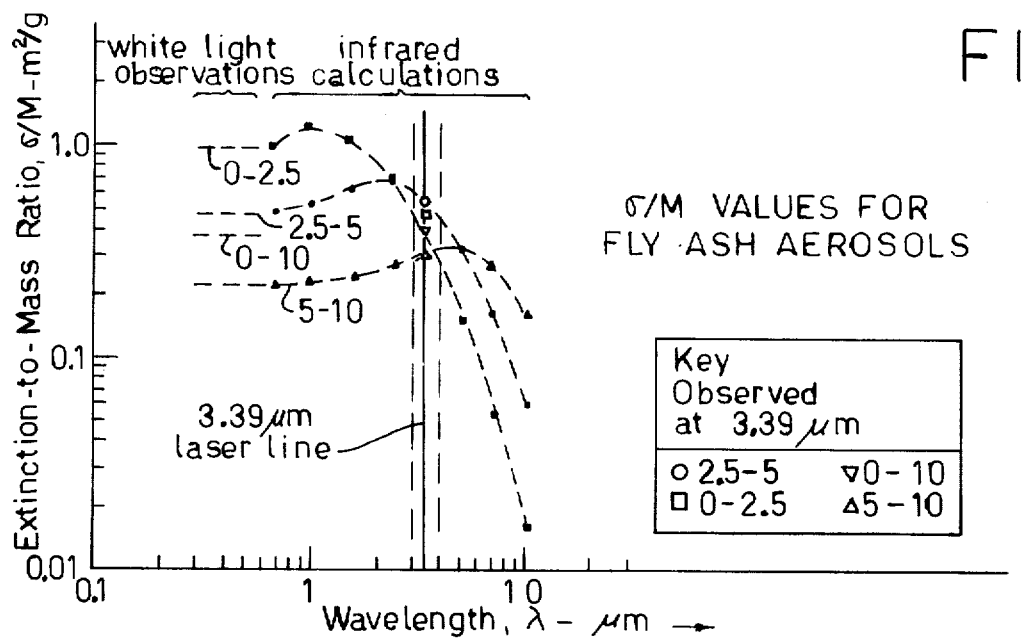
FIG. 1 are curves computed from scattering theory based on measured particle size distributions showing the dependence of the extinction coefficient-to-mass concentration ratio of fly ash aerosols on particle size and wavelength of the energy source.

Reference first is made to FIG. 1 wherein a series of curves of extinction coefficient-to-mass concentration ratio ($\sigma$/M) for different size distributions of fly ash particles as a function of wavelength are shown. As shown on the curves, four size fractions of fly ash were employed in the development thereof, including the size fractions represented by the diameter ranges of 0–2.5, 2.5–5, 5–10 and 0–10 $\mu$m. In FIG. 1 computational results for the extinction coefficient-to-mass concentration ratio ($\sigma$/M) as a function of wavelength for three of the four fly-ash particulate size fractions (0–2.5, 2.5–5 and 5–10 $\mu$m) are shown, together with experimentally determined white-light $\sigma$/M values for all four fractions. As seen in FIG. 1, the experimentally determined white-light $\sigma$/M values are in good agreement with the $\sigma$/M values computed at 0.7 $\mu$m. (Four observed values of $\sigma$/M at a wavelength of 3.39 $\mu$m also are shown in FIG. 1, which values are discussed in greater detail below.)

The data presented in FIG. 1 show that $\sigma$/M generally becomes smaller at longer wavelengths, with the greatest decrease occuring with the smaller size fraction. At a wavelength of 10 $\mu$m, the dependence of $\sigma$/M on particle size is just reversed from that in the visible wavelength region, with $\sigma$/M increasing with increasing particle size. It is apparent that a wavelength region exists where $\sigma$/M is substantially independent of particle size. For the illustrated fly ash fractions, this region exists between wavelengths of 3 to 4 $\mu$m. Among the four fractions, $\sigma$/M values vary by a factor of 4.4 at the visible wavelength, whereas the variability is within a factor of approximately 1.6 at the infrared region of 3 to 4 $\mu$m. As used, here and in the claims, operation of the radiant energy source at a wavelength at which the extinction coefficient-to-mass concentration ratio is "substantially insensitive to" of "substantially independent of" particle size, or variations in particle size, is intended to include factors between, say, 1 to 2.

It here will be noted that the infrared computations presented in FIG. 1 assumed that the particulate refractive index was invariant over the wavelength region and that the scattering particles were spherical shaped and nonabsorbing. An infrared transmissometer operating at a wavelength of 3.39 $\mu$m has been constructed and based upon transmittance readings of generated fly ash aerosols obtained using the same, $\sigma$/M ratios for the four fractions were calculated and are plotted in the curves of FIG. 1. These 'observed' infrared $\sigma$/M values are in good agreement with the theoretically computed values.

Figure 2:
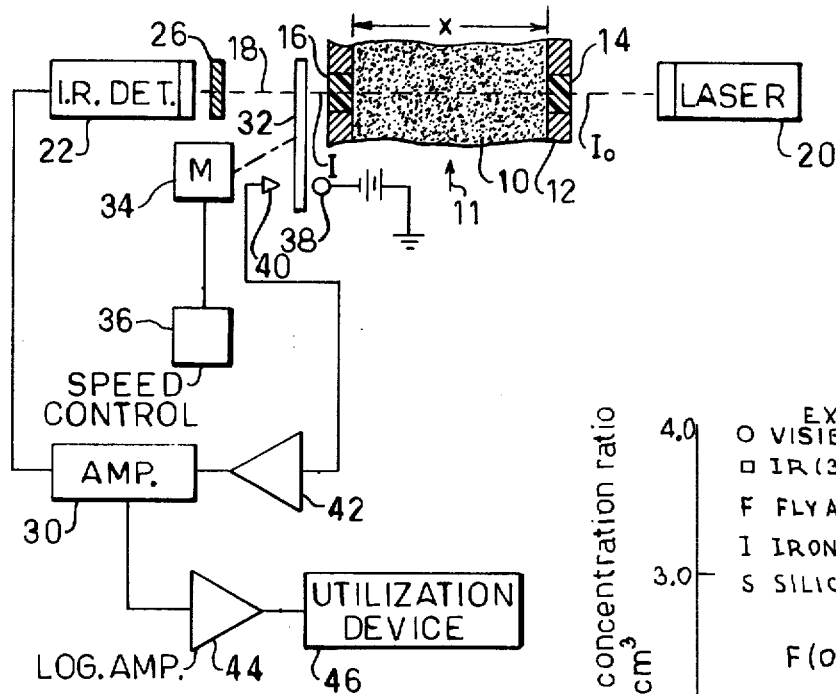
FIG. 2 is a block diagram showing of a transmissometer for monitoring the mass concentration of fly ash and other aerosol pollutants emitted from a source thereof.

A system for monitoring particulate mass concentration of emissions from a stationary source embodying the present invention is shown in FIG. 2, to which figure reference now is made. The gaseous medium containing the particulate material 10 flows in the direction of arrow 11 through a conduit, such as a stack, 12, a fragmentary portion of which is shown in FIG. 2. Windows 14 and 16 are provided in the stack walls for transmission of a beam 18 of electromagnetic radiation from an infrared laser 20 to an infrared detector 22 of a receiver through the stream of particle-containing gas along a path of length x through the particulate stream. In the illustrated arrangement a helium-neon laser is shown which includes an output at the wavelength of 3.39 μm. Filter 26 passes the beam 18 but substantially prevents other wavelength energy from entering the detector 22. Any suitable infrared detector 22 may be used including, for example, a pyroelectric having a substantially linear dynamic response.

An amplifier 30 responsive to the detector 22 output amplifies the signal from the detector. Due to the low signal-to-noise ratio of the detector output a tuned lock-in type amplifier preferably is employed. For such use, a rotating disk 32, having alternate transparent and opaque sectors is positioned in the path of the beam for chopping the same as the disk is rotated by a motor 34. The speed of the motor is controlled by speed control unit 36. A synchronous signal for the amplifier for synchronizing the operation thereof with the detector output is provided by a light source 38 and photodiode 40 positioned at opposite sides of the disk. The photodiode output is amplified by amplifier 42, and the amplifier output is supplied as a synchronous signal to the tuned lock-in amplifier 30.

As seen in FIG. 2, Io represents the intensity of the beam 18 entering the conduit 12, I represents the intensity thereof after passing through the path length x of particulate material flowing through the conduit. Transmittance, T, is defined as the ratio of I/Io. That is, $$T = I/Io \tag{1}$$

Also, by definition, $$T = I/Io = e^{-\sigma x} \tag{2}$$

wherein:
$\sigma$ = the extinction coefficient (1/meters)
Equation (2) may be rewritten as follows:

$$T = e^{-(\sigma/M)Mx} \tag{3}$$

wherein:
M = mass concentration of the particulate material.
If the extinction coefficient-to-mass concentration ratio, $\sigma/M$, is constant for all particles observed, equation (4) may be rewritten as follows:

$$T = e^{-KM} \tag{4}$$

wherein:
K = a constant dependent upon the constants $\sigma/M$ and x. Therefore:

$$KM = \ln 1/T, \text{ and} \tag{5}$$

$$M = 1/K \cdot \ln 1/T \tag{6}$$

In FIG. 2, the amplified signal from the tuned lock-in amplifier is supplied to a logarithmic amplifier 44 having an output related to ln 1/T which, as seen in equation (6), is directly related to mass concentration of particulate material 10 flowing through the conduit 12. The amplifier 44 output may be supplied to a meter, recorder, or other such utilization device 46, as desired.

The invention is not limited to mass concentration measurements of fly ash. Experiment indicates that the mass concentration of other pollutant aerosols, such as iron oxide and silica (silicon dioxide) may be monitored using the present method and apparatus. In addition to the above-mentioned fly ash aerosols, two-wave-length transmission observations have been made using one size fraction of ironoxide and three size fractions of silica. The silica fractions included 5, 10 and 15 μm maximum particle diameters. These experiments involved the use of transmissometers that employ helium-neon laser 20 operating at 3.39 μm, and visible light. Extinction-to-mass measurements also depend upon the specific gravity of the aerosol. Therefore, to compare results of materials of different specific gravity, the volume concentration (mass concentration weighted for the specific gravity) has been employed.

Figure 3:
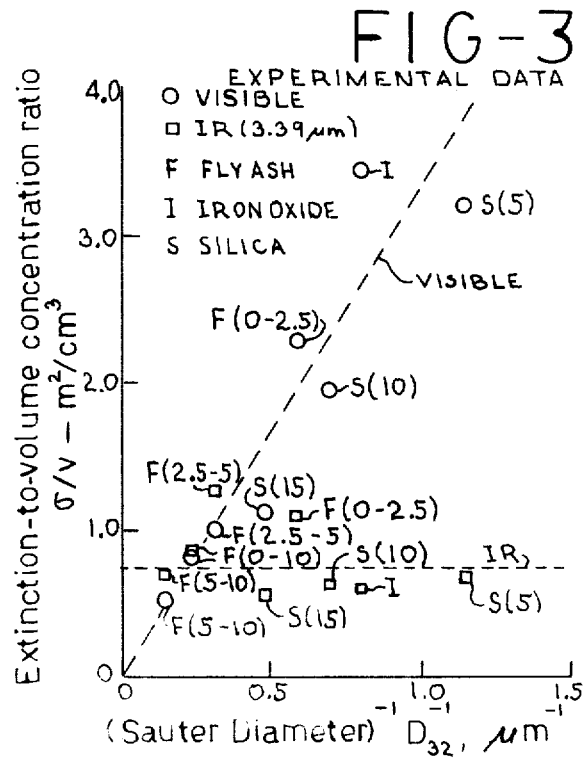
FIG. 3 are curves showing experimental extinction-to-volume concentration ratios as a function of particle size for visible and infrared wavelengths.

FIG. 3, to which reference now is made, is a plot of the experimentally derived extinction-to-volume concentration $\sigma/v$ ratios of the particulate material (the four fly ash fractions, the three silica fractions and the one iron oxide fraction) as a function of Sauter diameter. The visible wavelength $\sigma/v$ values clearly show a strong dependence on particle size, while the infrared wave-length values are substantially independent of particle size. The plot shows therefore, that the infrared transmission is a good indicator of aerosol volume concentration, regardless of particle type or size. The observed particle types were of different shapes, and probably of different absorption coefficients. Therefore, the data indicate that if the particulate emission is of a given chemical nature (e.g. specific gravity), but with varying particle sizes, then measurements with the transmissometer of FIG. 2, operating at a wavelength of 3.39 μm, are good indications of mass concentration.

The invention having been described in detail in accordance with the requirements of the Patent Statutes, various changes and modifications will suggest themselves to those skilled in this art and it is intended that such changes and modifications shall fall within the spirit and scope of the invention recited in the appended claims.

I claim:
1. A system for use in monitoring mass concentration of a stream of particulate material for which the particle size distribution may vary, said system comprising,
a source of electromagnetic radiation for directing a beam of radiation through the particulate stream,
radiation receiver means for measuring radiation from said radiation source transmitted through said particulate stream,
said radiation source being operated at substantially a single wavelength at which the extinction coefficient-to-mass concentration ratio of the particulate material stream is substantially independent of variations in particle size for the range of particle sizes in the stream whereby the output from the receiver means provides a measure of mass concentration of the particulate material stream.

2. A system as defined in claim 1 wherein said particulate material stream comprises particulate pollutants and said radiation source and receiver means operate at an appropriate infrared energy wavelength.

3. A system as defined in claim 1 wherein said radiation receiver means has a logarithmic response characteristic.

4. A system for use in monitoring mass concentration of a stream of particulate material for which the particle size distribution may vary, said particulate material stream comprising particulate pollution ranging in particle size up to a maximum of approximately 10 μm, said system comprising, a source of electromagnetic radiation for directing a beam of radiation through the particulate stream, radiation receiver means for measuring radiation from said radiation source transmitted through said particulate stream, said radiation source being operated at substantially a single wavelength at which the extinction coefficient-to-mass concentration ratio of the particulate material stream is substantially independent of variations in particle size for the range of particle sizes in the stream whereby the output from the receiver means provides a measure of mass concentration of the particulate material stream, said radiation source and receiver means operating between 3 and 4 μm.

5. A system as defined in claim 4 wherein said receiver means includes a pyroelectric detector.

6. A system for use in monitoring mass concentration of a stream of particulate material for which the particle size distribution may vary, said system comprising, a source of electromagnetic radiation comprising a helium-neon laser operating at a wavelength of substantially 3.39 μm for directing a beam of radiation through the particulate stream, radiation receiver means for measuring radiation from said radiation source transmitted through said particulate stream, said radiation source being operated at substantially a single wavelength at which the extinction coefficient-to-mass concentration ratio of the particulate material stream is substantially independent of variations in particle size for the range of particle sizes in the stream whereby the output from the receiver means provides a measure of mass concentration of the particulate material stream.

7. A method of measuring mass concentration of particulate material carried by a gaseous medium flowing through a conduit wherein the particulate material is of particle size distribution that can vary, said method comprising, employing radiant energy source and radiant energy detector means to obtain a measure of radiant energy transmission through said particle-containing gaseous medium, operating said radiant energy source and detector means at a single wavelength at which the extinction coefficient-to-mass concentration ratio is substantailly insensitive to particle size changes within the range of particle sizes flowing through the conduit whereby the measure of radiant energy transmitted provides a measure of mass concentration of particles independent of variations of particle sizes during said flow.

8. A method as defined in claim 7 wherein said radiant energy source and detector means are operated at a single infrared wavelength.

9. A method of measuring mass concentration of pollutant particulate material carried by a gaseous medium flowing through a conduit wherein the particulate material is of particle size distribution that can vary, said method comprising, employing radiant energy source and radiant energy detector means to obtain a measure of radiant energy transmission through said particle-containing gaseous medium, operating said radiant energy source and detector means at a single infrared wavelength between approximately 3 to 4 μm at which the extinction coefficient-to-mass concentration ratio is substantially insensitive to particle size changes within the range of particle sizes flowing through the conduit whereby the measure of radiant energy transmitted provides a measure of mass concentration of particles independent of variations of particle sizes during said flow.

10. A method as defined in claim 9 wherein the radiant energy source employed comprises a helium-neon laser operating at a wavelength of substantially 3.39 μm.

* * * * *